United States Patent

Nagubandi

Patent Number: 4,743,403
Date of Patent: May 10, 1988

[54] PROCESS FOR PREPARING ORGANO-SULFONIUM HALIDES

[75] Inventor: Sreeramulu Nagubandi, New City, N.Y.

[73] Assignee: Stauffer Chemical Co., Westport, Conn.

[21] Appl. No.: 584,972

[22] Filed: Mar. 1, 1984

[51] Int. Cl.$^4$ .................................. C07C 149/06
[52] U.S. Cl. .............................. 260/543 H; 260/544 K
[58] Field of Search ....................... 260/543 H, 544 K; 568/18

[56] References Cited

U.S. PATENT DOCUMENTS 2,252,081  8/1941  Lieber ................................. 568/18
3,101,265  8/1963  Smutny et al. ........................ 71/98

OTHER PUBLICATIONS

Kirk–Othmer, *Encyclopedia of Chemical Technology*, 3rd ed. (1983), vol. 22, pp. 233–235.
March, Jerry, *Advanced Organic Chemistry: Reactions, Mechanisms, and Structure*, (1968), p. 343.
Kirk–Othmer, *Encyclopedia of Chemical Technology*, 2nd ed., vol. 4 (1964), Interscience, publ. pp. 386–387.
Christie, J. Joseph et al., *J. Org. Chem.*, vol. 48 (1983), pp. 2531–2534.
Kirk–Othmer, *Encyclopedia of Chemical Technology* (1955), vol. 13, pp. 440–441.
Matzner, Markus et al., *Chemical Reviews*, vol. 64 (1964), pp. 645 and 657.
House, Herbert O., *Modern Synthetic Reactions*, 2nd ed. (1972), W. A. Benjamin, publ. pp. 452–453.

*Primary Examiner*—Donald B. Moyer
*Assistant Examiner*—L. Hendriksen
*Attorney, Agent, or Firm*—Hensley M. Flash; Harry A. Pacini

[57] ABSTRACT

Disclosed is a process for preparing organo-sulfonium halide of the formula

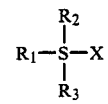

wherein X is an halide, $R_1$, $R_2$ and $R_3$ are the same or different and are selected from the group consisting of: alkyl having 1 to 24 carbon atoms, inclusive; allyl having 2 to 24 carbon atoms, inclusive; alkenyl having 2 to 24 carbon atoms, inclusive; alkynyl having 2 to 24 carbon atoms, inclusive; aryl having 6 to 24 carbon atoms, inclusive; and wherein said alkyl, allyl, alkenyl, alkynyl and aryl are optionally substituted with a group that is inert to organo-sulfides comprising: reacting an alcohol, e.g. methanol, with an halide derivative which when reacted with an organo-sulfide forms an organo-sulfonium halide, e.g., thionyl halide, sulfuryl halide and carbonyl halide; and then adding an organo-sulfide, e.g., dimethyl sulfide, to the above reaction mixture with agitation while allowing the gas formed to be eliminated so that the organo-sulfonium halide, e.g., trimethyl sulfonium halide, is formed. This process can take place in the presence of an insert solvent, e.g., methylene chloride.

11 Claims, No Drawings

PROCESS FOR PREPARING ORGANO-SULFONIUM HALIDES

BACKGROUND OF THE INVENTION

1. Field of the Invention

This invention relates to a process for preparing organo-sulfonium halides. More particularly, it relates to a process for preparing trialkylsulfonium halides.

2. Related Art

Organo-sulfonium halides are useful in the preparation of pesticides and herbicides. Specifically, the sulfonium salts of N-phosphonomethylglycine have been found to be particularly effective herbicides against various types of grasses and other unwanted weeds.

In the preparation of the trialkylsulfonium salts of N-phosphonomethylglycine, the starting material is trialkylsulfonium hydroxide which is derived from the salt, trialkylsulfonium halide, in a number of different ways including electrolysis.

Sulfonium salts are, in part, known compounds, and methods for preparing all of these salts are shown in the art. U.S. Pat. No. 3,101,265 (Smutny et al., Aug. 20, 1963) discloses plant growth-modifying compositions comprising trialkylsulfonium salts and describes therein a method for preparing these salts. This method involves the reaction of a thioether, RSR' with a suitable aliphatic derivative of the anion of an inorganic acid i.e., an aliphatic halide, R''X or an aliphatic sulfate, R'''R''''SO$_4$.

The Encyclopedia of Chemical Technology, Kirk-Othmer, Volume 13, pages 440–441 describes the conventional synthesis of sulfonium compounds by the reaction of alkyl halides with sulfides, disulfides, thioaldehydes or thioketones.

However, novel ways of preparing these salts are sought because of their importance. It is an object of the present invention to provide an alternative method of producing organo-sulfonium salts and, in particular, trialkylsulfonium halides.

Other objects and advantages of the present invention are shown throughout the specification.

SUMMARY OF THE INVENTION

In accordance with the present invention, it has now been discovered that an organo-sulfonium halide can be prepared by reacting an alkylhaloformate with an organo-sulfide preferably with agitation while allowing the gas formed to be eliminated so that the organo-sulfonium halide is formed.

This invention further comprises a process for preparing an organo-sulfonium halide in which an alcohol is first reacted with an halide derivative which when reacted with an organo-sulfide forms an organo-sulfonium halide and then reacting the product of this first step with an organo-sulfide preferably accompanied by agitation while allowing the gas formed to be eliminated so that the organo-sulfonium halide is formed.

DETAILED DESCRIPTION OF THE INVENTION

The present invention comprises a process for preparing an organo-sulfonium halide. This process comprises the step of reacting an alkylhaloformate with an organo-sulfide preferably with agitation while allowing the gas formed to be eliminated so that the organo-sulfonium halide is formed.

This invention further comprises a process for preparing an organo-sulfonium halide in which an alcohol is first reacted with an halide derivative which when reacted with an organo-sulfide forms an organo-sulfonium halide and then reacting the product of the first step with an organo-sulfide. This second step is preferably accompanied by agitation while allowing the gas formed to be eliminated so that the organo-sulfonium halide is formed and remains in the reactor.

The organo-sulfonium halides prepared by this invention can be of various configurations. A preferred organo-sulfonium halide is of the formula:

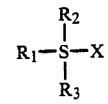

wherein X is an halide, $R_1$, $R_2$ and $R_3$ are the same or different and are selected from the group consisting of: alkyl having 1 to 24 carbon atoms, inclusive; allyl having 2 to 24 carbon atoms, inclusive; alkenyl having 2 to 24 carbon atoms, inclusive; alkynyl having 2 to 24 carbon atoms, inclusive; aryl having 6 to 24 carbon atoms, inclusive; and wherein said alkyl, allyl, alkenyl, alkynyl and aryl are optionally substituted with a group that is inert to the organo-sulfide used in this process. The halide X can be chloride, bromide, iodide or fluoride. Chloride is particularly preferred.

A particularly preferred organo-sulfonium halide prepared according to this invention is a trialkylsulfonium halide, e.g., trimethylsulfonium chloride, which results when $R_1$, $R_2$ and $R_3$ are methyl groups and X is a chloride group.

The alkylhaloformate used in the present invention can be prepared by reacting an alcohol with a carbonyl halide as represented by the following equation:

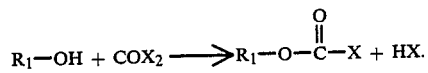

A preferred alkylhaloformate is methylchloroformate which is prepared by reacting methanol with phosgene.

The organo-sulfide used in the present invention can be of various configurations. A preferred organo-sulfide is of the formula:

wherein $R_2$ and $R_3$ are defined as stated above in the formula for the preferred organo-sulfonium halide. A particularly preferred organo-sulfide is a dialkyl sulfide, e.g., dimethyl sulfide, which results when $R_2$ and $R_3$ are methyl groups.

The following equation illustrates the reaction of the alkylhaloformate with the organo-sulfide to form the organo-sulfonium halide.

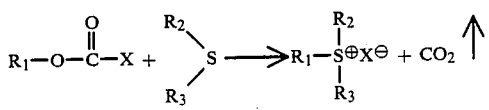

As can be seen from this equation, the choice of the R groups of the reactants will determine the particular organo-sulfonium halide formed.

In the process of this invention an alcohol is first reacted with an halide derivative which halide derivative when reacted with an organo-sulfide forms the organo-sulfonium salt. This halide derivative can be of various configurations, however a preferred specie can be selected from the group consisting of thionyl halide, sulfuryl halide and carbonyl halide. The chloride is particularly preferred.

The process of this invention can be carried out in the presence of an inert solvent. This inert solvent is preferably one that does not contain an hydroxy group. Methylene chloride is a preferred solvent.

The following generalized equation illustrates the process of this invention:

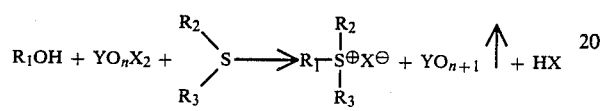

X, $R_1$, $R_2$ and $R_3$ are defined as stated above in the formula for the preferred organo-sulfonium halide. Y can be either carbon or sulfur and n is either the integer 1 or 2.

The reaction between the alkylhaloformate and the organo-sulfide can be carried out with agitation. This agitation aids the reaction and aids in the elimination of the gaseous reaction product from the reactor. However, agitation is only preferred and is not essential to the process.

The temperature condition for the process of this invention as illustrated by the generalized equation above is not critical. The reaction between the alcohol, $R_1OH$, and the halide derivative, $YO_nX_2$, is exothermic, therefore heating is not preferred. This process has been carried out at temperatures from about 0° C. up to about 30° C., however there is nothing to prevent this process from being carried out at temperatures outside this range.

The concentration of the various compounds used in the processes of this invention are generally not critical except that the alcohol concentration should be equal to or less than the concentration of the halide derivative. Preferred concentrations of alcohol to halide derivative are 1:1 and 1:1.1, however any concentration of alcohol equal to or less than that of the halide derivative can be used. The preferred concentration of the organo-sulfide is one mole equivalent. Lower concentrations of organo-sulfide can affect the yield of the end product negatively and higher concentrations may not be economical, however other concentrations can be used. In general, the concentrations chosen will depend upon the amount of organo-sulfonium halide desired to be prepared with a minimum of operational difficulties.

The following Example illustrates certain embodiments of the present invention but should not be construed in a limiting sense. The scope of protection sought is set forth in the claims which follow the Example.

EXAMPLE

To a solution of methanol (10.1 ml, 0.25 moles) in methylene chloride (100 ml), thionyl chloride (20.05 ml, 0.275 moles) was added at 0° C., followed by the addition of a solution of dimethyl sulfide (20.2 ml, 0.275 moles) in methylene chloride (50 ml).

The temperature was allowed to rise to room temperature and the mixture was stirred over 72 hours. An oily layer was formed in the reactor. This layer was separated and then evaporated to obtain 19.5 g (70% yield) of the desired trimethylsulfonium chloride.

The product was identified by analysis including NMR and mas spectroscopy.

What is claimed is:

1. A process for preparing an organo-sulfonium halide comprising:
   reacting an alkylhaloformate with an organo-sulfide forming the organo-sulfonium halide.

2. The process of claim 1 further comprising agitating the alkylhaloformate and the organo-sulfide during their reaction to allow the gas formed to be eliminated.

3. The process of claim 1 wherein the reaction takes place in the presence of an inert solvent.

4. The process of claim 3 wherein the inert solvent is methylene chloride.

5. The process of claim 1 wherein the alkylhaloformate is prepared by reacting an alcohol with a carbonyl halide.

6. The process of claim 1 wherein the alkylhaloformate is methylchloroformate.

7. The process of claim 1 wherein the organo-sulfide is a dialkyl sulfide.

8. The process of claim 7 wherein the dialkyl sulfide is dimethyl sulfide.

9. The process of claim 8 wherein the alkylhaloformate is methylchloroformate.

10. The process of claim 2 wherein the alkylhaloformate is methylchloroformate, the organo-sulfide is dimethyl sulfide and the reaction takes place in the presence of an inert solvent.

11. The process of claim 10 wherein the inert solvent is methylene chloride.

* * * * *